(12) United States Patent
Regensburger et al.

(10) Patent No.: US 12,159,355 B2
(45) Date of Patent: Dec. 3, 2024

(54) VIRTUAL ENHANCEMENT OF A CAMERA IMAGE

(71) Applicant: Siemens Healthcare GmbH, Erlangen (DE)

(72) Inventors: Alois Regensburger, Poxdorf (DE); Amilcar Alzaga, Schönbrun im Steigerwald (DE)

(73) Assignee: Siemens Healthineers AG, Forchheim (DE)

( * ) Notice: Subject to any disclaimer, the term of this patent is extended or adjusted under 35 U.S.C. 154(b) by 127 days.

(21) Appl. No.: 17/750,572

(22) Filed: May 23, 2022

(65) Prior Publication Data

US 2022/0392173 A1  Dec. 8, 2022

(30) Foreign Application Priority Data

Jun. 4, 2021 (DE) .................... 10 2021 205 688.1

(51) Int. Cl.
| | |
|---|---|
| *G06T 19/00* | (2011.01) |
| *A61B 1/00* | (2006.01) |
| *A61B 1/313* | (2006.01) |
| *G06T 7/60* | (2017.01) |

(52) U.S. Cl.
CPC ...... *G06T 19/006* (2013.01); *A61B 1/000095* (2022.02); *A61B 1/000096* (2022.02); *A61B 1/0005* (2013.01); *A61B 1/3132* (2013.01); *G06T 7/60* (2013.01); *G06T 2207/10068* (2013.01); *G06T 2207/20084* (2013.01); *G06T 2210/21* (2013.01); *G06T 2210/41* (2013.01); *G06T 2210/62* (2013.01)

(58) Field of Classification Search
None
See application file for complete search history.

(56) References Cited

U.S. PATENT DOCUMENTS

| 9,547,940 B1 | 1/2017 | Sun et al. |
| 2021/0093391 A1* | 4/2021 | Poltaretskyi ........... G16H 50/70 |

* cited by examiner

*Primary Examiner* — Yi Wang
(74) *Attorney, Agent, or Firm* — Lempia Summerfield Katz LLC

(57) ABSTRACT

According to a method for virtual enhancement of a camera image, a camera image depicting an object is generated. A geometric description of a virtual auxiliary object as a surface in space and a pose of the auxiliary object with respect to the object are specified, wherein the auxiliary object separates part of the object from the rest of the object. An enhanced image is generated based on a superimposition of the camera image with a representation of the auxiliary object depending on the geometric description and the pose of the auxiliary object by a computing unit and displayed on a display device. The enhanced image is generated and displayed in such a way that the auxiliary object has a spatially variable transparency.

16 Claims, 3 Drawing Sheets

VIRTUAL ENHANCEMENT OF A CAMERA IMAGE

The present patent document claims the benefit of German Patent Application No. 10 2021 205 688.1, filed Jun. 4, 2021, which is hereby incorporated by reference in its entirety.

TECHNICAL FIELD

The present disclosure relates to a method for virtual enhancement of a camera image, wherein a camera image depicting an object is generated, and to a corresponding apparatus for virtual enhancement of a camera image and to a computer program product.

BACKGROUND

The use of enhanced reality, also referred to as augmented reality, to support the performance of medical interventions, in particular surgical interventions, is known per se. In this context, it is possible to superimpose tissue parts to be removed, vascular trees, or other anatomical structures on a camera image as virtual objects.

However, it has been found that even appropriately trained specialists have difficulty in perceiving the depth of such superimpositions. This, for example, has the result that the person performing the medical intervention sometimes perceives the superimposed virtual objects at locations that are different from those where they may actually be represented. This problem also occurs when the registration of the camera image to the superimposed virtual structures is intrinsically error-free, so that the person performing the procedure is provided with misleading spatial information about hidden anatomical structures or trajectories for incision guidance. This reduces the added value provided by superimposition of the virtual objects.

SUMMARY AND DESCRIPTION

It is an object of the present disclosure to disclose a possibility for virtually enhancing a camera image by which the visual perception of a virtual object that is spatially related to a real object is improved.

The scope of the present disclosure is defined solely by the appended claims and is not affected to any degree by the statements within this summary. The present embodiments may obviate one or more of the drawbacks or limitations in the related art.

The disclosure is based on the idea of representing a virtual auxiliary object, which separates part of the object from the rest of the object, with a spatially variable transparency on an object on a camera image.

One aspect of the disclosure relates to a method for virtual enhancement of a camera image. In this context, a camera image depicting an object is generated, e.g., by a camera system. A geometric description of a virtual auxiliary object as a surface in space, (e.g., as a two-dimensional manifold with or without a border in three-dimensional space), and a pose of the auxiliary object with respect to the object are specified. In this context, the auxiliary object separates part of the object from the rest of the object. An enhanced image is generated based on a superimposition of the camera image with a representation of the auxiliary object depending on the geometric description and depending on the pose of the auxiliary object by a computing unit and displayed on a display device. The enhanced image is generated, (e.g., by the computing unit), and displayed on the display device in such a way that the auxiliary object has a spatially variable transparency.

In other words, in addition to the geometric description and the pose of the auxiliary object with respect to the object, a function is also specified that defines a transparency value on the surface of the auxiliary object as a function of the spatial position on the auxiliary object.

Virtual enhancement of the camera image may be understood as superimposition of the camera image with the representation of the virtual auxiliary object. In this context, it is also possible to refer to augmented reality. The enhanced image may also be referred to as an augmented image.

Virtual enhancement of the camera image by superimposition of the representation of the auxiliary object is in particular used for visual characterization or highlighting of part of the object that is separated from the rest of the object by the auxiliary object. As a result, in particular a spatial position of the part of the object in the object and a boundary of the part of the object in the form of the auxiliary object is represented visually.

A person viewing the enhanced image on the display device may then, for example, act on the object with a tool, wherein the viewer may perceive the representation of the auxiliary object as an orientation aid. In this way, the viewer may be assisted in the removal of soft tissue from the object, e.g., during dissection or resection. The object may be a human or animal organ or another type of voluminous anatomical object. The part of the object that is separated by the auxiliary object from the rest of the object is in particular partially located inside the object and may be located completely inside the object or contain sections of a surface of the object. Therefore, the object without the part of the object corresponds to the rest of the object.

At this point, it should be pointed out that the action on the object, in particular by the tool, for example for the surgical removal of the part of the object from the object, is not part of the method. In other words, the method does not include any surgical acts. Rather, the method acts of the method may be performed in the context of a surgical intervention, but do not themselves constitute surgical acts—they only assist the surgeon in the performance of the surgical acts. In particular, it is possible for all acts of the method to be performed without any simultaneous action being taken on the object by the tool.

The camera system may include one or more cameras. The camera system may also, for example, be integrated in an endoscope. The introduction of the endoscope into a cavity of a human or animal body is likewise not part of the method but takes place before the method is performed.

The camera system may also be embodied as a stereoscopic camera system. The method acts are then performed for each partial image, for example.

The display device in particular contains a screen or a display. The display device may also contain a visual output device that a user may wear on the head. Such a device is also referred to as an HMD ("head mounted display"). Other terms are, for example, video glasses, AR glasses, AR headset, etc.

The virtual auxiliary object is specified as a surface in space, e.g., as a two-dimensional manifold in three-dimensional space. This in particular means that the surface of the virtual auxiliary object may be curved, but this is not necessarily the case. The geometric shape of the auxiliary object, which is defined by the geometric description, may be any shape, e.g., it is not restricted to regular geometric figures or the like. For example, the geometric description may be constructed based on simulations, models or image data from imaging methods performed in advance, such as X-ray-based methods or magnetic resonance tomography methods, etc. In this way, the geometric description of the auxiliary object may be defined such that an object to be removed, (e.g., a tumor), is spatially separated in the object from the rest of the object by the auxiliary object. Thus, the auxiliary object may define an incision area for a surgeon.

In addition, other anatomical circumstances, in particular the position and course of blood vessels or vascular trees in the object may also be taken into account in the construction of the geometric description. The geometric description may advantageously be constructed such that no vessels extend through the surface of the auxiliary object. In this way, a surgeon may be prevented from damaging vessels that are not visible in the real camera image when cutting along the surface of the auxiliary object.

For the superimposition of the camera image with the representation of the auxiliary object, it may be possible to register the geometric description of the auxiliary object with the camera image in order to provide a correct anatomical position according to the construction of the auxiliary object. Such registration methods are known per se.

In particular, the geometric description of the auxiliary object and the pose of the auxiliary object are such that the surface of the auxiliary object intersects a surface of the object. In other words, the geometric shape and the pose of the auxiliary object with respect to the object define a surface contour on the surface of the object, wherein the surface contour corresponds to an intersecting line of the auxiliary object with the surface of the object.

The pose of the auxiliary object may refer to a combination of the position of the auxiliary object and the orientation of the auxiliary object. Thus, the pose includes the position and the orientation of the auxiliary object with respect to the object. The pose being specified with respect to the object may be understood as meaning that the position and orientation are stored directly with respect to a corresponding position and orientation of the object. However, the position and orientation of the auxiliary object may also be given in a reference coordinate system in which the position and orientation of the object is also known. The specification of absolute coordinates and absolute orientations in the reference coordinate system of both the auxiliary object and the object also indirectly specifies the pose of the auxiliary object with respect to the object.

The transparency of the auxiliary object may assume values between a minimum transparency value and a maximum transparency value, (e.g., in a range of 0 to 1), wherein the maximum transparency value corresponds to a completely transparent representation and the minimum transparency value corresponds to a completely opaque representation. Transparency may also be regarded as the reciprocal of opacity. Here, transparency and opacity may be understood as referring to light in the visible spectral range, e.g., in the wavelength range from 380 nm to 780 nm. In other words, transparency may also be understood as transmittance or average transmittance for light from the visible spectral range.

Each point on the surface of the auxiliary object may be defined in terms of corresponding three-dimensional coordinates in a specified coordinate system. Transparency is then a non-constant function of these three-dimensional spatial coordinates when viewed over the entire auxiliary object.

Spatially variable transparency enables a person viewing the enhanced image to be provided with directional information, which makes a depth position of the corresponding points on the auxiliary object intuitively perceptible. Thus, the method provides an additional information level that goes beyond the geometric shape of the auxiliary object and through which depth perception may be improved when viewing the superimposed image.

Trained surgeons may have many years of experience in the field of surgical interventions without the assistance of enhanced reality capabilities. In this context, surgeons learn to follow real anatomical structures into the depths of the tissue and to make incisions along these anatomical structures. The anatomical structures may be so-called embryonic layers, e.g., cell layers that are formed during human or animal embryogenesis and through which, consequently, no blood vessels extend. Hence, by following the embryonic layer, the surgeon is able to make incisions without damaging blood vessels. Thus, the embryonic layers or other anatomical structures are used to define incision areas and intersection lines. These anatomical structures may be visible to the surgeon as a subtle shimmer through the surrounding semi-transparent tissue. In this context, the closer the anatomical structures, and in particular the embryonic layers, are to the surface of the surrounding tissue, the easier they are to identify.

However, anatomical guide structures, such as those represented by embryonic layers, are not always available, e.g., in the case of dissection of tumors in voluminous organs, such as the liver.

Thus, to a certain extent, the spatially variable transparency of the auxiliary object in the method enables simulation of a virtual anatomical structure or a virtual embryonic layer which the surgeon may use for orientation even if no corresponding anatomical structures are present in the actual object or the anatomical structures are only very poorly identifiable.

Due to the surgeon's training and experience in following embryonic layers or other anatomical structures into the depths of the tissue with appropriate tools, the method, and in particular the representation of the auxiliary object with spatially variable transparency, appeals to the cognitive abilities of the surgeon, consciously or even unconsciously. Thus, the disclosure makes it easier for the surgeon to perceive the relevant information from the enhanced image correctly; in particular depth perception is improved.

In various embodiments, the idea on which the disclosure is based may also be understood as artificially evoking an intuitive understanding that the surgeon has when viewing real anatomical structures in situations in which corresponding anatomical structures are not present or are not sufficiently easily identifiable.

In various embodiments, the spatially variable transparency of the auxiliary object may also be specifically modeled on an embryonic layer. In other words, the auxiliary object is simulated as an artificial embryonic layer in order to determine the spatially variable transparency.

For this purpose, for example, a reference transparency curve of embryonic layers may be specified. In order to determine the reference transparency curve, corresponding reference measurements may be carried out on real embryonic layers.

A point on the auxiliary object may be assigned a depth corresponding to a clearance between the respective point and the surface contour corresponding to the intersection line between the auxiliary object and the surface of the object.

In this context, the depth is in particular positive inside the object, equal to zero on the surface contour and negative outside the object. In this context, the clearance may correspond to a length of the shortest connecting line between the corresponding point and the surface contour. In the case of curved surfaces, this line may not be straight. Other clearances or metrics may also be used as the clearance.

According to at least one embodiment of the method, the enhanced image is generated and displayed in such a way that the transparency is a function of the depth of the point of the auxiliary object.

The spatially variable representation of the transparency as a function of depth may give the viewer an impression of the direction in which the auxiliary object extends into the interior of the object, as would also in particular be the case with real embryonic layers. This enables the viewer to have particularly intuitive perception and particularly good depth perception.

According to at least one embodiment, the transparency value increases with increasing depth.

In this context, the transparency value may be continuous, continuous in sections, and/or constant in sections.

In other words, the transparency value for a first point on the surface for the description of the auxiliary object is smaller than the transparency value for a second point on the surface for the description of the auxiliary object if the first point is on the surface contour and the second point is inside the object. This may, but does not necessarily have to, apply to all pairs of corresponding points. For example, this may also only apply when the depth of the second point is greater than or equal to a specified threshold value.

In this way, the appearance of an embryonic structure may be reproduced particularly well. Increasing transparency with increasing depth means the auxiliary object becomes less visible in depth than on the surface. However, the decrease in visibility with depth need not necessarily be as great as would be the case with real anatomical structures. As a result, the information content conveyed may be further increased by the enhanced image and also increased in comparison to a real anatomical structure.

According to at least one embodiment, the transparency value is constant when the depth is greater than or equal to a specified maximum depth.

In other words, all points on the auxiliary object with a depth greater than or equal to the specified maximum depth have a specified constant transparency value, which may correspond to the maximum transparency value, (e.g., 1).

The transparency value on the surface contour may be constant, for example correspond to the minimum transparency value, in particular 0.

According to at least one embodiment, the auxiliary object has a section which is located outside the object and is in particular in contact with the surface contour.

In other words, the auxiliary object is represented in such a way that the section of the auxiliary object appears to protrude from the surface of the object. This achieves better identifiability for the viewer.

In particular, the surface for the geometric description of the auxiliary object may be differentiated on the surface contour, in particular on each point of the surface contour.

In other words, the surface of the auxiliary object is regular, at least locally on the surface contour, so that there are no corners or edges on the surface contour. The result of this is that the spatial course of a further section inside the object which is in contact with the surface contour from the inside may be inferred from the spatial course of the section arranged outside the object. As a result, a more intuitive the directional information on the surface is provided even more intuitively.

According to at least one embodiment, the transparency value is constant in the section located outside the object.

For example, the transparency value in the section may correspond to the minimum transparency value, (e.g., 0), or to another constant transparency value.

Thus, the section located outside the object may be represented as a band or strip with constant transparency and/or constant width.

According to at least one embodiment, a further geometric description of a volume area on the surface of the object is specified, wherein the volume area includes at least part of the surface contour. The enhanced image is generated based on a superimposition of the camera image with the representation of the auxiliary object and a representation of the volume area depending on the further geometric description. The enhanced image is generated in such a way that the volume area is represented as partially transparent.

The fact that the volume area is arranged on the surface may be understood as meaning that part of the surface delimits the volume area. Thus, the volume area may be understood as being a layer on the surface.

Thus, the representation of the volume area corresponds to a simulation of the actual object on part of the surface of the object. In this context, the volume area hides the actual object at the corresponding position in the enhanced image. Because the volume area is represented as partially transparent, (such as with a, e.g., constant, transparency value that is smaller than the maximum transparency value and greater than the minimum transparency value), a visual impression may be created that makes the volume area appear to be a semi-transparent liquid or glass layer on the surface of the object.

Because the volume area includes at least part of the surface contour, the auxiliary object, (e.g., the surface of the auxiliary object), extends at least partially through the volume area. Due to the partially transparent representation of the volume area, the viewer is easily able to identify the course of the auxiliary object through the volume area so that the directional information in the upper area close to the surface of the object may be provided even more efficiently.

According to at least one embodiment, an anatomical structure of the object, in particular a real anatomical structure of the object, is detected based on the camera image and/or based on further sensor data relating to the object. The geometric description of the auxiliary object is generated based on the detected anatomical structure and/or the pose of the auxiliary object with respect to the object is determined based on the detected anatomical structure.

In this context, the further sensor data may be at least partially generated by ultrasonic examination of the object and/or by confocal microscopy and/or by hyperspectral imaging.

Thus, in such embodiments, the auxiliary object is generated in such a way that it reflects the position of the actual anatomical structure that may be ascertained in advance by the further sensor data and/or by the camera image.

For example, by the computing unit, a trained artificial neural network may be applied to the camera image and/or the further sensor data in order to detect the anatomical structure and, in particular, to determine the shape and position of the anatomical structure.

Thus, in corresponding embodiments, the real anatomical structure is reproduced in the form of the auxiliary object, thus enabling better identifiability or visibility for the viewer.

A further aspect of the disclosure also relates to an apparatus for virtual enhancement of a camera image. The apparatus has a camera system configured to generate a camera image depicting an object. The apparatus has a memory element which stores a geometric description of a virtual auxiliary object as a surface in space and a pose of the auxiliary object with respect to the object. In this context, the auxiliary object separates part of the object from the rest of the object. The apparatus has a display device and a computing unit configured to generate an enhanced image based on a superimposition of the camera image with a representation of the auxiliary object depending on the geometric description and the pose of the auxiliary object and to display it on the display device. The computing unit is configured to generate the enhanced image and display the enhanced image on the display device such that the auxiliary object has a spatially variable transparency.

According to at least one embodiment of the apparatus, the apparatus has an endoscope, (e.g., a laparoscope), containing the camera system.

According to at least one embodiment, the apparatus contains a sensor system configured to generate further sensor data relating to the object. The computing unit is configured to detect an anatomical structure of the object based on the sensor data or based on the sensor data and the camera image and to generate the geometric description of the auxiliary object based on the detected anatomical structure and to store it on the memory element and/or to determine the pose of the auxiliary object with respect to the object based on the detected anatomical structure and to store it on the memory element.

In this context, the sensor system may have an ultrasonic sensor system, in particular an ultrasonic transmitter or an ultrasonic probe, a confocal microscope, or a hyperspectral imaging system, e.g., a hyperspectral camera.

Further embodiments of the apparatus follow directly from the various embodiments of the method and vice versa. In particular, an apparatus maybe configured to perform a method, or it performs such a method as disclosed herein.

A further aspect of the disclosure relates to a computer program with instructions. When the instructions are executed by an apparatus, in particular by the computing unit of the apparatus, the instructions cause the apparatus to perform a method as disclosed herein.

A further aspect of the disclosure relates to a computer-readable storage medium that stores a computer program.

The computer program and the computer-readable storage medium may also be understood as respective computer program products with the instructions.

A computing unit may be understood to be a data processing device; thus, the computing unit may process data for performing computing operations. These may also include operations for performing indexed accesses to a data structure, for example, a look-up table (LUT).

The computing unit may contain one or more computers, one or more microcontrollers, one or more integrated circuits, (e.g., one or more application-specific integrated circuits (ASICs)), one or more field-programmable gate arrays (FPGAs), and/or one or more systems on a chip (SoCs). The computing unit may also contain one or more processors, e.g., one or more microprocessors, one or more central processing units, (CPUs), one or more graphics processing units (GPUs), or, in particular, one or more digital signal processors (DSPs). The computing unit may also include a physical or a virtual network of computers or another one of the units named.

In various exemplary embodiments, the computing unit includes one or more hardware and/or software interfaces and/or one or more memory units.

If, in the context of the present disclosure, there is a reference to the fact that a component of the apparatus, in particular the computing unit or the display device, is configured, embodied, designed or the like, to execute or implement a specific function to achieve a specific effect or to serve a specific purpose, this may be understood as meaning that, beyond the principle or theoretical usability or suitability of the component for this function, effect or this purpose, the component is specifically and actually capable of executing or implementing the function, achieving the effect or serving the purpose by a corresponding adaptation, programming, physical embodiment etc.

Further features of the disclosure may be derived from the claims, the figures, and the description of the figures. The features and feature combinations mentioned above in the description and the features and feature combinations mentioned below in the description of the figures and/or shown in the figures may be encompassed by the disclosure not only in the specified combination in each case, but also in other combinations. In particular, the disclosure also encompasses embodiments and feature combinations which do not have all the features of a claim as originally formulated. Moreover, the disclosure encompasses embodiments and feature combinations that extend beyond or deviate from the feature combinations described in the back references in the claims.

The disclosure is explained in more detail below with reference to specific exemplary embodiments and associated schematic drawings. In the figures, identical or functionally identical elements may be provided with the same reference numbers. The description of identical or functionally identical elements may not necessarily be repeated with respect to different figures.

DETAILED DESCRIPTION

Figure 1:
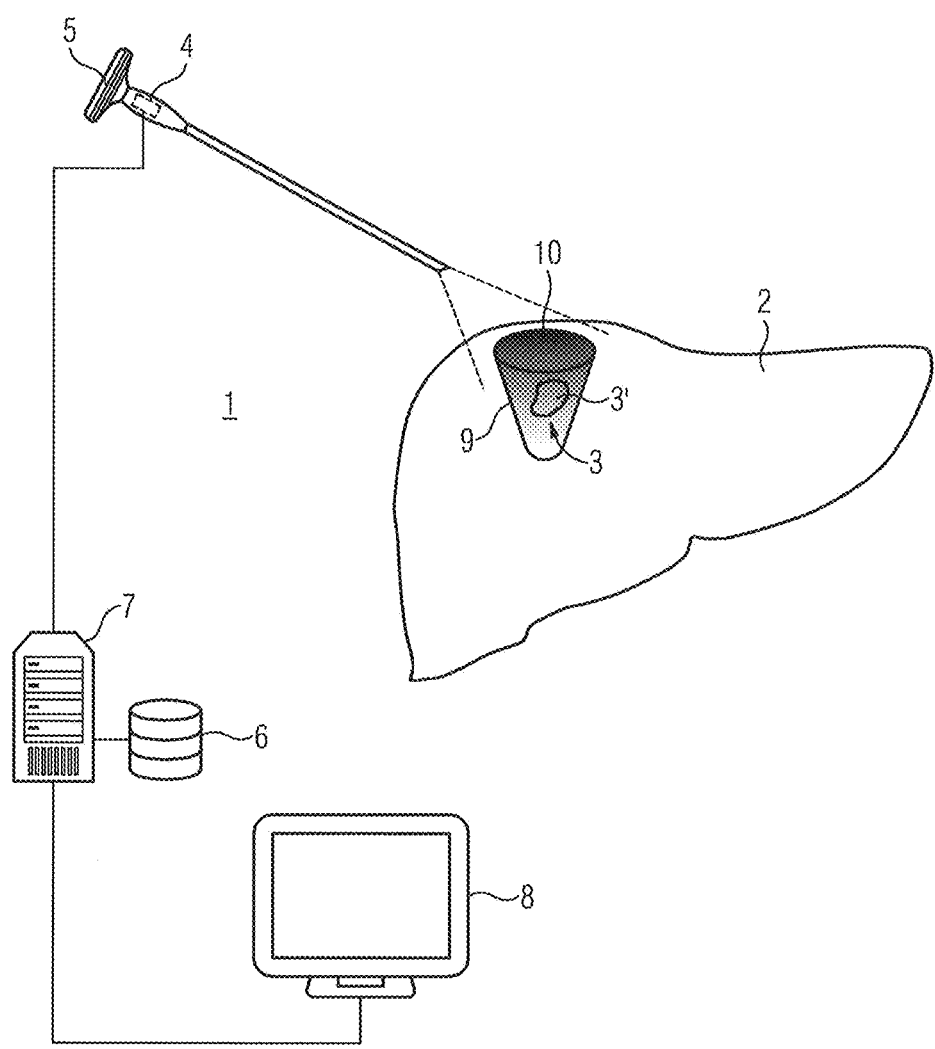
FIG. 1 depicts a schematic representation of an apparatus according to an embodiment.

FIG. 1 is a schematic representation of an exemplary embodiment of an apparatus 1 for virtual enhancement of a camera image.

The apparatus 1 has a camera system 4, which may be integrated in an endoscope 5, for example. The apparatus 1 also has a computing unit 7 with a communication link to the camera system 4 such that the camera system 4 may transmit image data or camera images to the computing unit 7. The apparatus 1, (e.g., the computing unit 7), also has a memory element 6 and a display device 8 connected to the computing unit 7 so that the computing unit 7 may actuate the display device 8 in order to display image information to a user (not depicted).

FIG. 1 also shows an object 2, (e.g., a human organ, in particular, a liver). In the object 2, a further object to be removed 3', (e.g., a tumor or the like), is located in a part 3 of the object 2.

After the camera system 4 has been positioned and aligned such that it is able to depict an area of the object 2, for example, by appropriately introducing the endoscope 5 into the abdominal cavity of the human, the apparatus 1 may perform a method for virtual enhancement of a camera image.

For this purpose, the camera system 4 may generate a camera image, which depicts the object 2 in the corresponding field of view of the camera system 4 and transmit it to the computing unit. The computing unit 7 may generate an enhanced image 13 (see FIG. 2 to FIG. 4) by superimposing a representation of an auxiliary object 9 on the camera image. The computing unit 7 may then actuate the display device 8 to display the enhanced image 13.

In this context, the memory element 6 stores a description of the virtual auxiliary object 9 as a surface in space and a pose of the auxiliary object 9 with respect to the object 2. In this context, the auxiliary object 9 is shaped and positioned such that it separates the part 3 of the object 2 from the rest of the object 2. In this context, the auxiliary object 9 in particular intersects a surface of the object 2, so that a surface contour 10 is created on the surface of the object.

In this context, the computing unit 7 generates the enhanced image 13 such that the auxiliary object 9 is depicted on the display device 8 with a spatially variable transparency.

Examples of the representation are explained below with reference to the figures FIG. 2 to FIG. 4 each of which show a schematic example of an enhanced image 13.

Figure 2:
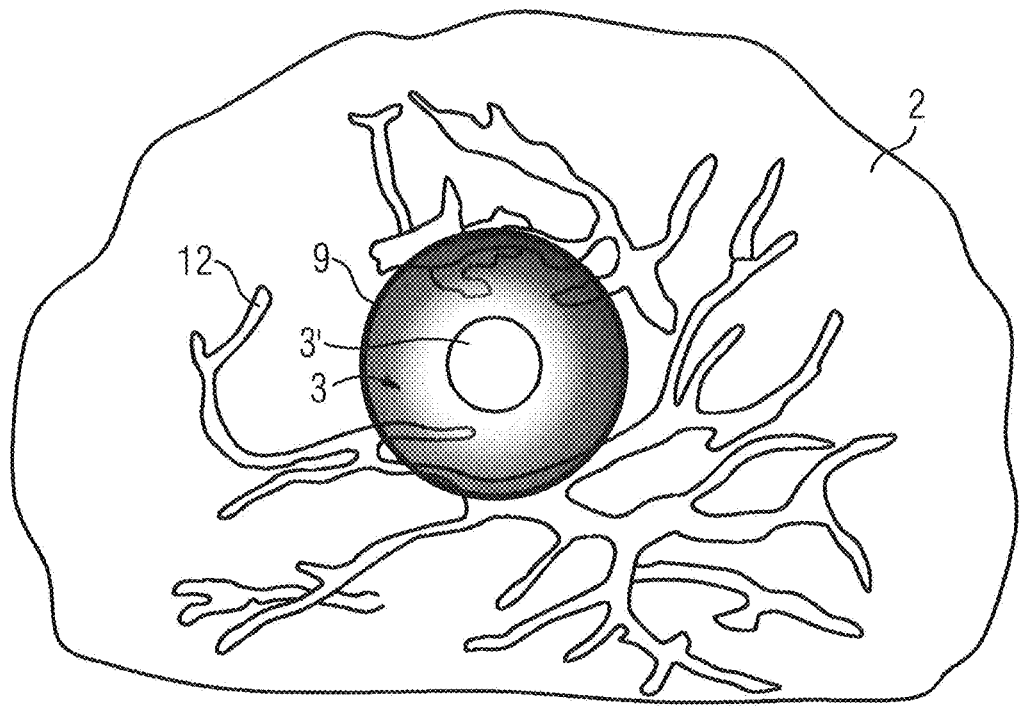
FIG. 2 depicts a schematic representation of an enhanced image according to an embodiment.
Figure 3:
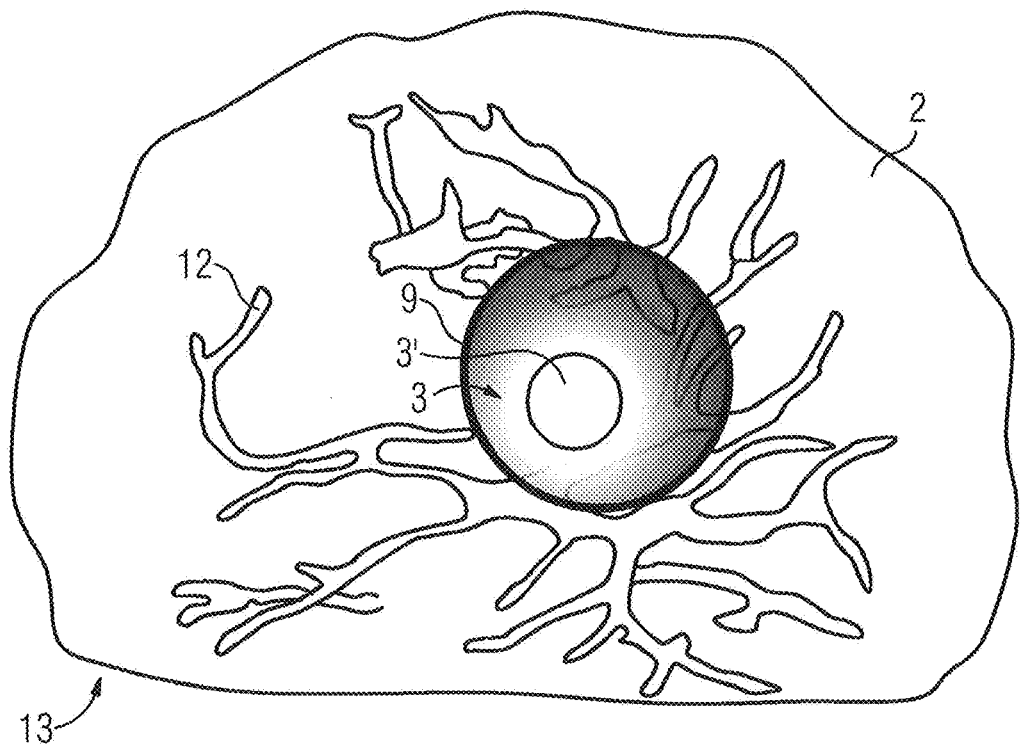
FIG. 3 depicts a further schematic representation of an enhanced image according to an embodiment.
Figure 4:
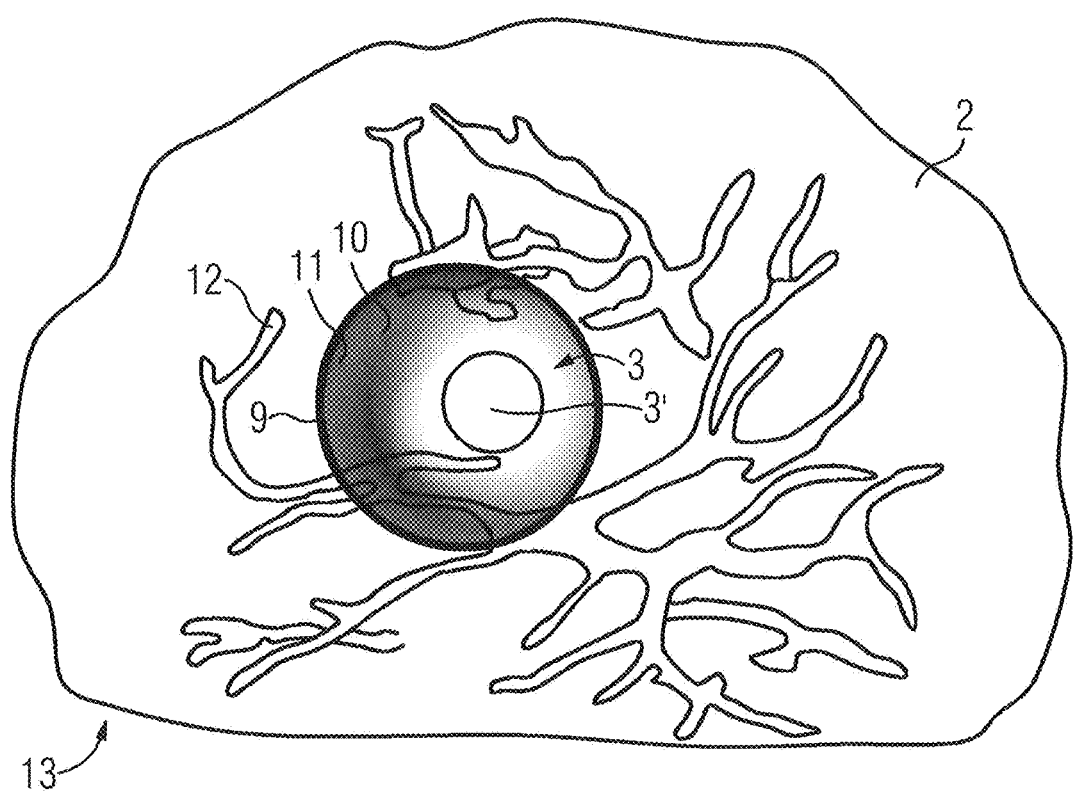
FIG. 4 depicts a further schematic representation of an enhanced image according to an embodiment.

Figures FIG. 2 to FIG. 4 depict the further object 3' in the part 3 of the object 2 as a circle or ellipse in each case. The auxiliary object 9 has, for example, the approximate shape of a circular cone or a circular cone with a rounded tip or the like. However, other, in particular far more complex and/or asymmetrical shapes of the auxiliary object 9 are also possible. Figures FIG. 2 to FIG. 4 also depict, by way of example, a vascular tree 12 in the object 2. The geometric shape and position of the auxiliary object 9 may advantageously be selected such that the auxiliary object 9 is not in contact with any vessels of the vascular tree 12.

On the other hand, the shape of the auxiliary object 9 may also be less complex. For example, the auxiliary object 9 may have the shape of a plane or another non-enclosed surface. The shape of the auxiliary object 9 may also be composed of a plurality of planes or non-enclosed surfaces.

As depicted in FIG. 3 and FIG. 4, for example, the transparency of the auxiliary object 9 increases with increasing depth in the object 2 such that the auxiliary object 9 is more clearly visible on the surface of the object 2 than in the depth of the object 2. This provides the viewer with improved depth perception reminiscent of the appearance of an embryonic layer.

The auxiliary object 9 may optionally be specified such that a section 11 (see FIG. 3) of the auxiliary object 9 protrudes from the surface of the object 2 so that even more intuitive directional information as to how the surface of the auxiliary object 9 extends into the interior of the object 2 may be achieved.

As described, in particular with regard to the figures, the disclosure provides a viewer with a more natural impression, in particular with respect to depth perception.

After many years of training, surgeons may be very skilled at following fine anatomical structures into the depths of an organ. An example of such structures are embryonic layers that may be used to guide the surgical incision area. They subtly shimmer through the tissue so that, when trained surgeons view these structures, they may intuitively identify the direction to take their instruments in order to follow these structures.

In various embodiments and variants of the disclosure, virtual anatomical structures may be rendered as augmented reality so that they appear similar to real anatomical structures. In particular, the appearance of embryonic layers may be simulated. The surgical trajectory then appears approximately as a surgeon would see a genuine embryonic layer, which may then be followed deeper into the tissue.

The auxiliary object superimposed on the camera image adds not only a line to the tissue surface, but also a transparency gradient that allows the viewer to perceive the direction in which the superimposed surface extends into the tissue. Rendering may take place from the viewer's perspective so that changing this perspective, and possibly the virtual ambient light conditions, may help the viewer to make a better estimation of the direction of the virtual anatomical structure.

In various embodiments, the auxiliary object may be depicted in such a way that it a protrudes a small distance from the tissue surface, (e.g., about 2 mm). This allows the surgeon to make a better estimation of the direction of the surgical planes into the tissue. In various embodiments, the tissue may also be rendered so that the uppermost area, (e.g., the uppermost 3 mm), appears semi-transparent.

In various embodiments, real anatomical structures, such as embryonic layers visible close to the tissue surface, may be segmented. In some situations, these are difficult to identify with the naked eye. For example, a trained artificial neural network may be used to automatically identify these anatomical structures. The identification may be purely image-based or video-based or further data sources, such as intraoperative ultrasound, a registered preoperative model, or other contextual information about the patient may be used.

Optionally, advanced imaging methods, such as scanning the surface with confocal microscopy, or the integration of hyperspectral imaging functions may assist the segmentation or identification of the actual anatomical structure on the tissue surface. It is also possible for continuity constraints to be applied to assist segmentation. Embryonic planes are not punctiform objects but extend as curved lines along the visible tissue surface. Therefore, hidden parts of the embryonic planes may be interpolated, including by using geometric information from the preoperative or further intraoperative imaging. Optionally, selective contrast enhancement and/or artificial superimposition may be provided at the position of the anatomical structures in order to make them even more visible to the surgeon.

In a further embodiment, it is possible to determine the orientation of the embryonic layer or another anatomical structure, such as by estimating the local normal vector of the plane, e.g., based on video analysis, based on preoperative information and/or based on intraoperative imaging, for example, by ultrasound or confocal microscopy.

For example, superimposed artificial anatomical structures may be color-coded in order to indicate proximity to at-risk structures below the visible tissue surface.

The disclosure may enable visual pointers of a virtual world to be applied to real objects and vice versa. This enables a more natural impression to be achieved, false interpretations of the representation by the viewer to be avoided, and easier tracking of artificial and/or natural guide structures.

It is to be understood that the elements and features recited in the appended claims may be combined in different ways to produce new claims that likewise fall within the scope of the present disclosure. Thus, whereas the dependent claims appended below depend on only a single independent or dependent claim, it is to be understood that these dependent claims may, alternatively, be made to depend in the alternative from any preceding or following claim, whether independent or dependent, and that such new combinations are to be understood as forming a part of the present specification.

While the present disclosure has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A method for virtual enhancement of a camera image depicting an object, the method comprising:
   specifying, by a computing unit, a geometric description of a virtual auxiliary object as a surface in space and a pose of the auxiliary object with respect to the object, wherein the auxiliary object separates part of the object from a rest of the object;
   generating, by the computing unit, an enhanced image based on superimposition of the camera image with a representation of the auxiliary object depending on the geometric description and the pose of the auxiliary object; and
   displaying the enhanced image on a display device,
   wherein the enhanced image is generated and displayed in such a way that the auxiliary object has a spatially variable transparency, and
   wherein the spatial variable transparency is a function of a depth of a respective point of the auxiliary object within the object such that a transparency value of the auxiliary object changes with a change in depth of the auxiliary object at least until a specified maximum depth.

2. The method of claim 1,
   wherein the depth corresponds to a clearance between the respective point and a surface contour, and
   wherein the surface contour corresponds to an intersection line between the auxiliary object and a surface of the object.

3. The method of claim 2, wherein the transparency value increases with increasing depth.

4. The method of claim 2, wherein the transparency value is constant when the depth is greater than or equal to the specified maximum depth.

5. The method of claim 2, wherein the auxiliary object has a section located outside the object, and
   wherein the surface for the geometric description of the auxiliary object is configured to be differentiated on the surface contour.

6. The method of claim 5, wherein the transparency value is constant in the section located outside the object.

7. The method of claim 2, further comprising:
   specifying a further geometric description of a volume area on the surface of the object, wherein the volume area includes at least part of the surface contour,
   wherein the enhanced image is generated based on a superimposition of the camera image with the representation of the auxiliary object and a representation of the volume area depending on the further geometric description, and
   wherein the enhanced image is generated in such a way that the volume area is represented as partially transparent.

8. The method of claim 1, wherein the auxiliary object is simulated as an artificial embryonic layer in the object in order to determine the spatially variable transparency.

9. The method of claim 1, further comprising:
   detecting, by the computing unit, an anatomical structure of the object based on the camera image and/or based on further sensor data relating to the object; and
   generating the geometric description of the auxiliary object based on the detected anatomical structure and/or determining the pose of the auxiliary object with respect to the object based on the detected anatomical structure.

10. The method as claimed in claim 9, wherein the further sensor data is at least partially generated by ultrasonic examination of the object, by confocal microscopy, by hyperspectral imaging, or a combination thereof.

11. The method of claim 9, wherein, by the computing unit, a trained artificial neural network is applied to the camera image and/or the further sensor data in order to detect the anatomical structure.

12. An apparatus for virtual enhancement of a camera image, the apparatus comprising:
    a camera system configured to generate a camera image depicting an object;
    a memory element configured to store a geometric description of a virtual auxiliary object as a surface in space and a pose of the auxiliary object with respect to the object, wherein the auxiliary object separates part of the object from a rest of the object;
    a display device; and
    a computing unit configured to:
       generate an enhanced image based on a superimposition of the camera image with a representation of the auxiliary object depending on the geometric description and the pose of the auxiliary object; and
       display the enhanced image on the display device,
       wherein the enhanced image is generated and displayed on the display device such that the auxiliary object has a spatially variable transparency, and
       wherein the spatial variable transparency is a function of a depth of a respective point of the auxiliary object within the object such that a transparency value of the auxiliary object changes with a change in depth of the auxiliary object at least until a specified maximum depth.

13. The apparatus of claim 12, further comprising:
    an endoscope containing the camera system.

14. The apparatus of claim 13, wherein the endoscope is a laparoscope.

15. The apparatus of claim 12, further comprising:
    a sensor system configured to generate further sensor data relating to the object,
    wherein the computing unit is further configured to:
       detect an anatomical structure of the object based on the sensor data; and
       generate the geometric description of the auxiliary object based on the detected anatomical structure and/or determine the pose of the auxiliary object with respect to the object based on the detected anatomical structure.

16. A computer program stored on a non-transitory computer readable medium, wherein the computer program comprises instructions which, when executed by an apparatus, cause the apparatus to:
    specify a geometric description of a virtual auxiliary object as a surface in space and a pose of the auxiliary object with respect to an object, wherein the auxiliary object separates part of the object from a rest of the object;
generate an enhanced image based on superimposition of a camera image with a representation of the auxiliary object depending on the geometric description and the pose of the auxiliary object; and
display the enhanced image on a display device,
wherein the enhanced image is generated and displayed in such a way that the auxiliary object has a spatially variable transparency, and
wherein the spatial variable transparency is a function of a depth of a respective point of the auxiliary object within the object such that a transparency value of the auxiliary object changes with a change in depth of the auxiliary object at least until a specified maximum depth.

* * * * *